United States Patent [19]

Heinsohn et al.

[11] Patent Number: 5,215,908
[45] Date of Patent: Jun. 1, 1993

[54] PROCESS FOR RECOVERY AND PURIFICATION OF CHYMOSIN

[75] Inventors: Henry G. Heinsohn, Pacifica; Matthew B. Murphy, San Francisco, both of Calif.

[73] Assignee: Genencor International, Inc., Rochester, N.Y.

[21] Appl. No.: 869,838

[22] Filed: Apr. 16, 1992

Related U.S. Application Data

[63] Continuation of Ser. No. 365,944, Jun. 13, 1989.

[51] Int. Cl.$^5$ .............................................. C12N 9/64
[52] U.S. Cl. ..................................... 435/226; 435/225; 435/815
[58] Field of Search ............... 435/226, 225, 223, 815, 435/816; 426/36, 42

[56] References Cited

U.S. PATENT DOCUMENTS

| | | | |
|---|---|---|---|
| 2,339,931 | 1/1944 | Keil | 195/68 |
| 3,281,332 | 10/1966 | Munns et al. | 195/66 |
| 3,834,990 | 9/1974 | Werle et al. | 195/68 |
| 4,016,039 | 4/1977 | Schreiber | 195/66 R |
| 4,145,406 | 3/1979 | Schick et al. | 424/1 |
| 4,250,084 | 2/1981 | Trainin | 260/112 R |
| 4,259,319 | 3/1981 | Umezawa et al. | 424/117 |
| 4,264,738 | 4/1981 | Stepanov et al. | 435/222 |
| 4,332,717 | 6/1982 | Kanaoka et al. | 260/112 R |
| 4,461,833 | 7/1984 | Gordon | 435/183 |
| 4,471,053 | 9/1984 | Comi et al. | 435/226 |
| 4,568,488 | 2/1986 | Lee-Huang | 260/112 R |
| 4,666,843 | 5/1987 | Subramanian | 435/226 |
| 4,675,384 | 6/1987 | Dromard et al. | 530/364 |
| 4,684,723 | 8/1987 | Dove et al. | 530/351 |
| 4,687,740 | 8/1987 | Waite | 435/69 |
| 4,710,566 | 12/1987 | Kozarich et al. | 536/28 |
| 4,721,673 | 1/1988 | Uren et al. | 435/183 |
| 4,722,999 | 2/1988 | Handschumacher et al. | 530/412 |
| 4,743,551 | 5/1988 | Subramanian | 435/226 |
| 4,745,063 | 5/1988 | Birschbach | 435/226 |
| 4,752,578 | 6/1988 | Moore et al. | 435/68 |
| 4,757,008 | 7/1988 | Reverman | 435/94 |

FOREIGN PATENT DOCUMENTS 0123928 11/1984 European Pat. Off. .

OTHER PUBLICATIONS

Biotechnology Applications and Research (1985), Cheremisinoff, et al., eds., Technomic Pub., pp. 549–552.
Pharmacia Biotechnology Products Catalog 86 (1986) p. 93.
Franke, et al., J. of Ind. Microbiology, Suppl. No. 3 pp. 43–57.

Primary Examiner—Charles L. Patterson, Jr.
Attorney, Agent, or Firm—Burns, Doane, Swecker & Mathis

[57] ABSTRACT

This invention provides a method of recovering and purifying chymosin from fermentation used for microbial production of chymosin. The fermentation mixture is filtered to provide a filtrate containing the chymosin. The filtrate is first prepared by either adjusting it to a low pH, such as about 2 and/or adjusting the salt concentration of the filtrate to at least about 2M. The aqueous filtrate mixture is contacted with a phenyl-sepharose resin, which selectively binds the chymosin from the filtrate. The filtrate remaining after the contact with the phenyl-sepharose resin is discarded, and the phenyl-sepharose resin column is eluted with water or dilute salt solution to obtain substantially pure chymosin in a single elution step.

16 Claims, 1 Drawing Sheet

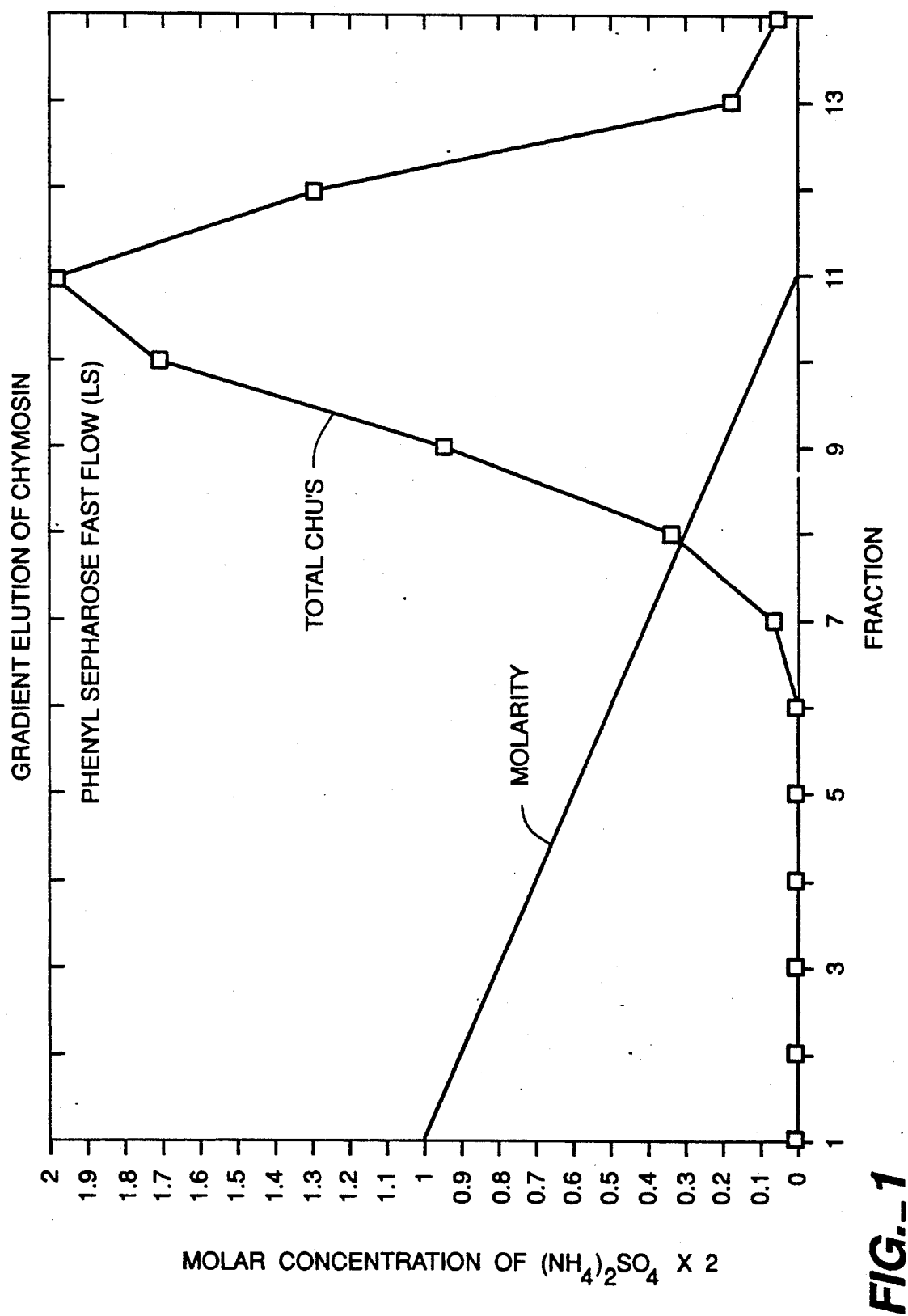
FIG._1

PROCESS FOR RECOVERY AND PURIFICATION OF CHYMOSIN

This application is a continuation of application Ser. No. 07/365,944, filed Jun. 13, 1989.

FIELD OF THE INVENTION

This invention relates to the recovery and purification of chymosin from aqueous mixtures of enzymes, particularly aqueous mixtures of enzymes produced by fermentation processes.

BACKGROUND OF THE INVENTION

Chymosin has been separated and purified using various techniques. For example, calf rennet or rennet extracts have been purified using blue dye affinity ligands, as in U.S. Pat. No. 4,666,843 to Subramanian or using a cellulose resin column, as in U.S. Pat. No. 4,745,063 to Birschbach. The same methods have been used to recover and purify microbially produced chymosin, as in U.S. Pat. No. 4,743,551 to Subramanian and U.S. Pat. No. 4,721,673 to Uren et al., respectively. The disclosures of these patents are incorporated herein by reference.

However, in industrial or commercial scale production of chymosin by microbial activity these methods of recovery and purification of chymosin are inadequate. For commercial scale industrial production, more efficient, more economical methods of recovering and purifying chymosin are needed. It is also essential that such processes be adaptable to economic scale-up for commercial production.

Of particular interest in the industrial microbial production of chymosin is the production of chymosin by fermentation of filamentous fungi which have been genetically modified to express and secrete chymosin, as disclosed in U.S. patent application Ser. No. 163,219 of Lawlis et al. filed Feb. 26, 1988, abandoned in favour of U.S. patent application Ser. No. 07/413,010 filed Sep. 25, 1989 incorporated herein by reference.

It is an object of this invention to provide efficient processes for the separation and purification of chymosin from aqueous mixtures of enzymes, particularly aqueous mixtures produced by fermentation or other microbial activity and particularly for commercial scale production of chymosin.

SUMMARY OF THE INVENTION

This invention is a method for separating chymosin from an aqueous mixture of enzymes by contacting the aqueous mixture with a phenyl-sepharose resin to bind the chymosin to the resin and separating the resin and the bound chymosin from the remainder of the aqueous mixture. The chymosin is then eluted from the resin with water or a dilute salt solution. Before contacting the aqueous mixture of enzymes with the phenyl-sepharose resin, the aqueous mixture is prepared for the resin contact in one of two ways. In one preparation, a concentrated salt solution is added to the aqueous mixture to increase the salt content of the mixture which enhances the effective binding of chymosin to the phenyl-sepharose resin. In another preparation, the pH of the aqueous mixture of enzymes is reduced to below about 3 before contacting the aqueous mixture of enzymes with the phenyl-sepharose resin.

BRIEF DESCRIPTION OF THE DRAWING

The drawing shows the elution of chymosin from phenyl-sepharose resin in response to salt concentration.

DESCRIPTION OF THE INVENTION

This invention is described in terms of aqueous mixtures of enzymes which contain chymosin. The method of this invention is particularly useful with aqueous mixtures of enzymes obtained from microbial expression where the chymosin is produced intracellularly or from microbial expression where the chymosin is produced in the cells and secreted from the cells. A preferred aqueous mixture of enzymes useful in this invention results from the fermentation of microbial expression hosts which secrete the chymosin resulting in extracellular chymosin. The method of this invention may also be used to separate chymosin from aqueous mixtures of enzymes obtained from other sources, such as from calf rennet extracts.

In one preferred method of carrying out the present invention, a fermentation broth, such as from fermentation of *Aspergillus Niger*, is treated with sulfuric acid to reduce the pH to about 2. About 1 to 2% by weight (based on the weight of the total mixture) of acetic acid is added to stop the fermentation and effect a substantially complete cell kill. Then ammonium hydroxide is added to bring the pH to about 5.9. The mixture then is diluted to about twice its original volume with water and subjected to filtration to remove cells debris and other solids. A salt, preferably sodium chloride, is added either before or after the filtration to bring the liquid filtrate to a salt concentration of about 2M. The pH is maintained at about 5.9 and the liquid filtrate is contacted with a phenyl-sepharose resin column. The chymosin binds to the resin while the other enzymes and the salt solution pass through the phenyl-sepharose resin column and are discarded. The resin column is then washed with 2M sodium chloride and 50 mM phosphate to maintain the pH at about 5.9. After washing, the chymosin is eluted from the phenyl-sepharose resin column with water or with dilute salt solution such as 50 mM phosphate. The chymosin is eluted in bulk; there is no need for a gradient or stepwise elution, because chymosin is the only predominant enzyme in such mixtures of enzymes which binds to the phenyl-sepharose resin. The chymosin produced by this process is substantially pure and usually food grade, which needs only to be diluted with water, filtered and treated with sodium chloride and preservative to conform the product to the desired specifications for sale as a final chymosin product ready for industrial use. The resin column is then washed with 0.1M to about 1M sodium hydroxide, then washed with water and is reused for another batch of prepared filtrate.

In another preferred method of carrying out the process of the present invention, the pH of the fermentation mixture is reduced to about 2 with sulfuric acid and about 1 to 2% by weight of acetic acid is added to stop the fermentation process and effect a cell kill. In this method, the pH of the mixture is maintained at about 2 while the mixture is filtered to remove the cell debris and other solids and produce a liquid filtrate containing a mixture of enzymes. After the filtrate is obtained from the filtration step, the pH is still maintained at about 2 while the filtrate is contacted with a phenyl-sepharose resin column. If desired, salts may be added to the filtrate before contacting the filtrate with the resin column. In some cases the addition of salt may enhance the binding of chymosin to the resin column. Examples of such salts are 0.5M ammonium sulfate or 0.5M sodium sulfate. Upon contact of the filtrate with the phenyl-sepharose resin column, the chymosin binds to the resin in the column while the other enzymes and the filtrate solution pass through the column and are discarded. The phenyl-sepharose resin column containing the bound chymosin is then washed with 0.2M sodium chloride solution. While the pH can be maintained at about 2 and raised to a desired level of about 5.9 after elution, it is preferred that the pH be raised at this point in the process to about 5.9 with a 0.2M phosphate solution. After the resin column has been washed and the pH adjusted, if desired, the chymosin is bulk eluted with water or a weak salt solution, such as 50 mM phosphate solution. As above, the eluted chymosin is essentially pure and can be used for food grade applications. The eluted chymosin is diluted to the desired concentration, sodium chloride and a preservative added, and the solution filtered to provide the desired commercial product. Also as above, the resin column is then washed with 0.1M to 1M sodium hydroxide and then water to prepare the resin column for reuse with another batch of prepared filtrate.

It will be recognized that the above descriptions are preferred methods of carrying out the process of the present invention and that numerous variations of the above methods can be made in the process following the teachings of this invention. The various process conditions can be altered and reagents used can be changed to provide various desired or optimum operating conditions for recovery of chymosin from any suitable aqueous mixture of enzymes containing chymosin. The essential feature of the process however, is the use of phenyl-sepharose resin. The phenyl-sepharose resin has been found to be uniquely active and selective for binding chymosin from aqueous mixtures containing numerous other components and enzymes. Sepharose resins having other functional groups, such as octyl, have not been found to have the desired chymosin selectivity. While the scope of this invention is not to be limited or interpreted by the following theory, it is believed that it is the phenyl functionality on the sepharose resin which provides the high degree of selectivity for the chymosin. The phenyl-sepharose resin has been found to be particularly useful in separating chymosin from a fermentation broth because a fermentation broth contains a wide range of other components, enzymes, and impurities. In contrast, such complex mixtures interfere with the action of anion and cation exchange resins, thereby rendering them ineffective in recovering chymosin from a fermentation broth.

It has been found quite surprising in the present invention that chymosin is essentially the only enzyme material present in a fermentation broth that will bind to the sepharose resin under low pH and/or high salt concentration conditions. Normally, a number of different enzymes and other materials will bind to sepharose type resins, then the desired enzyme is recovered as a fraction by sequential, partial or stepwise elutions by gradually changing the pH and/or salt concentration of the eluting liquid. In that standard method, each enzyme is eluted at a different time, producing separate fractions, one or more of which will contain the desired enzyme to be recovered. Fractional elution also usually produces overlap of the fractions produced so that the desired product elutions may be spread at least partially into adjacent fractions, which reduces the amount of the total desired product that can be recovered, at least at a desired high degree of purity. Such fractional elution processes are not efficient enough for economical commercial use in large scale separations.

In contrast to the above, it has been found in the process of this invention that chymosin is essentially the only component of a fermentation broth filtrate that binds to the phenyl-sepharose resin. Consequently, gradient or fractional elution is neither necessary nor desired in process of this invention; the chymosin can be bulk eluted. This process provides high recovery rates because the phenyl-sepharose resin removes at least about 95% by weight of the total chymosin from the fermentation broth filtrate. This process is efficient because the chymosin can be quickly eluted from the resin column in one step without the need for fractional elutions. The resulting chymosin product is at least about 90% by weight pure and can prepared for commercial use without further significant treatment to remove impurities. The commercial chymosin product is usually diluted to about 5 grams per gallon or about 1.5 grams/l chymosin, the salt (usually NaCl) concentration is normally brought up to about 18% and a preservative such as sodium benzoate is added. The final commercial product intended for food grade use usually is also subjected to a final filtration to remove any undesirable solids or particulates that may be present.

Phenyl-sepharose resins are a well-known class of resins, also known as cross-linked phenyl-agarose resins. "Phenyl-Sepharose CL-4Bn" is a trademark for cross-linked phenyl-agarose resins of Pharmacia Fine Chemicals, AB, and as used herein "phenyl-sepharose" refers to any cross-linked agarose resin having a sufficient phenyl functionality to effectively bind chymosin from aqueous solution or suspension.

The phenyl-sepharose resin can be used in particle form in bulk having particle size in a range of about 40 microns to about 400 microns and can be mixed with the aqueous mixture of enzymes to allow the chymosin to bind to the resin. The resin can then be separated from the aqueous solution, then eluted and recycled as described above. However, it is preferred that the phenyl-sepharose resin be used in the form of a packed column where the column contains particles of the resin having a particle size in the range of about 40 microns to about 400 microns.

As will be recognized by those skilled in the art, the acids, bases and salts referred to above in the description of the process of this invention can be changed or substituted with equivalent acids, bases or salts which provide the desired pH or the desired salt content without interfering with the operation of the phenyl-sepharose resin in this invention and which do not denature the chymosin. Also, as recognized by those skilled in the art, the pH values referred to above can be modified within certain ranges and still obtain the desired results. For example, the fermentation broth can be processed and filtered at a pH of less than about 6, but it is preferred that the pH be less than about 3 and it is most preferred that the pH be maintained in a range of about 2. Likewise, where the pH is preferably adjusted to about 5.9 in the process, the pH at those points in the process can range from about 5 to about 6 and preferably between about 5.5 and about 6. Similarly, the concentration of the concentrated salts can be varied to provide the desired result. It has been found that the chymosin binds best to the phenyl-sepharose resin in the presence of a concentrated salt solution of at least about 1 M and/or when the pH of the aqueous mixture is less than about 3. Normally, it is preferred to use sodium chloride because of its low cost; examples of other useful salts are $Na_2SO_4$ and $(NH_4)_2SO_4$. A preferred salt concentration of the solution is about 2M, although higher or lower molar concentration of salt in the aqueous mixture of enzymes, for example in the range between about 1M and 2M, can be effective in binding the chymosin to the phenyl-sepharose resin. In the elution step, it has been found that the chymosin can be easily eluted in a single or bulk elution from the phenyl-sepharose resin with water or with weak solutions of salt. It is believed that the chymosin binds best to the phenyl-sepharose resin when ion concentration in a salt solution is high and then is easily eluted when the ion strength of the chymosin on the phenyl-sepharose resin is reduced by eluting with water or dilute salt solution.

Having described the present invention in terms of the above preferred methods of carrying out the process of this invention and the variations thereof the invention is now illustrated with the following specific examples.

EXAMPLE 1

This example describes a chymosin recovery process to produce food grade chymosin. The chymosin is recovered from fermentation of an Aspergillus Niger var. awamori. The process is described in terms of a 3000 l fermenter and a broth harvest volume of about 2500 l. When fermentation is complete, the broth is inactivated by pH adjustment to 2.0–2.5 with sulfuric acid and addition of acetic acid. (See U.S. patent application Ser. No. 07/365,945, filed Jun. 13, 1989 by Lawlis et al., incorporated herein by reference.) The inactivation conditions are held for 1 hour at the fermentation temperature and with air flow. This inactivation achieves sufficient viable cell reduction for containment to be broken. After inactivation the pH is adjusted to 5.5 with ammonium hydroxide. The inactivation and subsequent pH adjustment will require about 125 kg of sulfuric acid, 25 kg of glacial acetic acid, and 80 l of 28% ammonium hydroxide solution.

The inactivated broth is filtered using a rotary vacuum drum filter. The broth is diluted 2.5× with deionized water (2500l to 6250 l). The diluted material is made 3% wt/vol with Manville Celite 545 and filtered through a Celite 545 precoat. The cake is washed to increase yields. The filtrate volume should equal the starting feed volume.

The filtrate is polished before the phenyl-sepharose resin contact step by using a two-step pad filtration. The filtrate is made 6% wt/vol NaCl and 1% wt/vol HyFlo Super Cel and is filtered through SEN Supra 200 filter pads. The first stage filtrate is collected and pressed using Supra 50 pads. No filter aid is used in the second stage filtration.

The clarified filtrate is passed through a 10l phenyl sepharose resin column ("FAST FLOW L.S.", 40–100 micron particle size, from Pharmacia Fine Chemicals, AB). After loading, the column is washed with 3 volumes (30 l) of 6% NaCl solution. The column is then bulk eluted with 4 column volumes (40 l) of 50 mM sodium phosphate buffer at pH 5.5. The eluted chymosin solution is made 17% NaCl for commercial food grade use.

EXAMPLE II

Using the same phenyl sepharose resin as in Example I, this example illustrates a gradient elution of the chymosin from the resin.

CONDITIONS:
11.4 ML PHENYL SEPHAROSE RESIN
LOADING AND ELUTION AT 5.0 ML/MIN

| # | DESC. | $(NH_4)_2SO_4$* | CHU/L | VOL. (ML) | TOTAL CHU | TOTAL MGS |
|---|---|---|---|---|---|---|
| 1 | START MAT. | 1 | 1.62 | 5000 | 8.10 | 105.30 |
| 2 | VOID + WASH | 1 | 0.03 | 5000 | 0.15 | 1.95 |
| 3 | CHANGE pH | 1 | 0.03 | 50 | 0.00 | 0.02 |
| 4 | FRACTION 1 | 1 | 0.03 | 10 | 0.00 | 0.00 |
| 5 | FRACTION 2 | 0.9 | NA | 10 | 0.00 | 0.00 |
| 6 | FRACTION 3 | 0.8 | NA | 10 | 0.00 | 0.00 |
| 7 | FRACTION 4 | 0.7 | 0 | 10 | 0.00 | 0.00 |
| 8 | FRACTION 5 | 0.6 | 0.12 | 10 | 0.00 | 0.02 |
| 9 | FRACTION 6 | 0.5 | 0.61 | 10 | 0.01 | 0.08 |
| 10 | FRACTION 7 | 0.4 | 6.48 | 10 | 0.06 | 0.84 |
| 11 | FRACTION 8 | 0.3 | 34.04 | 10 | 0.34 | 4.43 |
| 12 | FRACTION 9 | 0.2 | 93.9 | 10 | 0.94 | 12.21 |
| 13 | FRACTION 10 | 0.1 | 170.1 | 10 | 1.70 | 22.11 |
| 14 | FRACTION 11 | 0 | 198.4 | 10 | 1.98 | 25.79 |
| 15 | FRACTION 12 | 0 | 128.9 | 10 | 1.29 | 16.76 |
| 16 | FRACTION 13 | 0 | 17.34 | 10 | 0.17 | 2.25 |
| 17 | FRACTION 14 | 0 | 5.37 | 10 | 0.05 | 0.70 |
| 18 | COMPOSITE | | 50.02 | 140 | 7.00 | 91.04 |

(CHU = Chris. Hansen Unit)
*Gradient: 1M to 0, as shown on the drawing.

Total recovery of the chymosin is about 85% by weight. The drawing attached hereto shows the above elution of chymosin as a function of ammonium sulfate concentration and illustrates the ease of recovering the chymosin in a single elution.

EXAMPLE III

Using a filtrate similar to Example I, the capacity of the phenyl sepharose resin under the following conditions is:

| Conditions | Resin Capacity (mg chymosin/l resin) |
|---|---|
| 2 M NaCl, pH 5.8 | 3.79 |

| Conditions | Resin Capacity (mg chymosin/l resin) |
|---|---|
| 1 M (NH$_4$)$_2$SO$_4$, pH 2.0 | 7.32 |

This example illustrates that the preferred method for practicing this invention is at the low pH.

What is claimed is:

1. A method for separating chymosin from an aqueous mixture of enzymes by utilizing a phenyl-agarose column which method comprises:
   (a) preparing the aqueous mixture of enzymes so that chymosin will be essentially the only enzyme material that will bind to the phenyl-agarose column wherein the aqueous mixture is prepared by the process selected from the group consisting of:
      (1) the addition of a sufficient concentration of a salt; and
      (2) adjusting the pH to less than about 3;
   (b) contacting the aqueous mixture of enzymes with a phenyl-agarose resin for sufficient time to allow chymosin to bind to the resin;
   (c) separating the resin and bound chymosin from the aqueous mixture; and
   (d) eluting the chymosin from the resin.

2. A method according to claim 1 wherein in step (a) the aqueous mixture of enzymes is prepared by the addition of a sufficient concentration of a salt.

3. A method according to claim 2 wherein the added salt comprises an inorganic salt solution having a concentration of at least about 1M.

4. A method according to claim 1 wherein the elution step includes the use of a dilute salt solution having a concentration of no more than about 0.5M.

5. A method according to claim 1 wherein the beginning aqueous mixture of enzymes is formed in a fermentation step.

6. A method according to claim 1 wherein in step (a) the aqueous mixture of enzymes is prepared by adjusting the pH to less than about 3.

7. A method for separating chymosin from an aqueous mixture of enzymes comprising:
   (a) adjusting the pH of the aqueous mixture to less than about 3;
   (b) contacting the pH-adjusted aqueous mixture of enzymes with a phenyl-agarose resin for sufficient time to allow the chymosin to bind to the resin;
   (c) separating the resin and bound chymosin from the aqueous mixture; and
   (d) eluting the chymosin from the resin.

8. A method according to claim 7 wherein the resin and bound chymosin are washed before the elution step with a salt solution having a concentration of at least about 1M.

9. A method according to claim 7 wherein the elution step includes the use of a dilute salt solution having a concentration of no more than about 0.5M.

10. A method according to claim 7 wherein the beginning aqueous mixture of enzymes is from a fermentation step.

11. A method according to claim 8 wherein the beginning aqueous mixture of enzymes is from a fermentation step.

12. A method for separating chymosin from an aqueous mixture of enzymes comprising:
   (a) adding a sufficient amount of salt to the aqueous mixture of enzymes so as to provide a salt concentration in the aqueous mixture of at least 1M;
   (b) contacting the aqueous mixture from (a) above with a phenyl-agarose resin for sufficient time to allow chymosin to bind to the resin;
   (c) separating the resin and bound chymosin from the aqueous mixture; and
   (d) eluting the chymosin from the resin.

13. A method according to claim 12 wherein the pH of the aqueous mixture in step (a) is adjusted to less than about 3.

14. A method according to claim 13 wherein the resin and bound chymosin are washed before the elution step with a salt solution having a concentration of at least about 1M.

15. A method according to claim 14 wherein the elution step includes the use of a dilute salt solution having a concentration of no more than about 0.5M.

16. A method according to claim 15 wherein the beginning aqueous mixture of enzymes is from a fermentation step.

* * * * *

UNITED STATES PATENT AND TRADEMARK OFFICE
CERTIFICATE OF CORRECTION

PATENT NO. : 5,215,908
DATED : June 1, 1993
INVENTOR(S) : Henry G. Heinsohn and Matthew B. Murphy It is certified that error appears in the above-indentified patent and that said Letters Patent is hereby corrected as shown below:

IN THE DRAWINGS

In Fig. 1, after "$(NH_4)_2 SO_4$", delete "x2".

Col. 2, line 24, "Aspergillus Niger" should read -- Aspergillus niger --.

Col. 4, line 12, after "in" insert --the--.

Col. 4, line 32, "CL-4Bn" should read --CL-4B--.

Col. 5, lines 53-54, "Aspergillus Niger var. awamori" should read --Aspergillus niger var. awamori--.

Col. 6, line 3, "(25001" should read --(2500 1--.

Col. 6, line 15, "101" should read --10 1--

Col. 8, line 29, after "allow" insert --the--.

Signed and Sealed this

Twenty-third Day of August, 1994

Attest:

BRUCE LEHMAN

Attesting Officer

Commissioner of Patents and Trademarks